(12) United States Patent
Shin et al.

(10) Patent No.: US 10,695,584 B2
(45) Date of Patent: Jun. 30, 2020

(54) METHOD FOR MEASURING DEPTH PROFILE OF PARTICLE BEAM USING ACOUSTIC SIGNALS GENERATED BY THE PARTICLE BEAM

(71) Applicant: ELECTRONICS AND TELECOMMUNICATIONS RESEARCH INSTITUTE, Daejeon (KR)

(72) Inventors: Dong-Ho Shin, Daejeon (KR); Moon Youn Jung, Daejeon (KR); Seunghwan Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 240 days.

(21) Appl. No.: 15/833,706

(22) Filed: Dec. 6, 2017

(65) Prior Publication Data

US 2018/0154182 A1    Jun. 7, 2018

(30) Foreign Application Priority Data

Dec. 6, 2016 (KR) .................. 10-2016-0165324
Nov. 16, 2017 (KR) .................. 10-2017-0153300

(51) Int. Cl.
*A61N 5/10* (2006.01)
*G01T 1/29* (2006.01)
*G01H 11/08* (2006.01)
*G01H 9/00* (2006.01)

(52) U.S. Cl.
CPC .............. *A61N 5/1071* (2013.01); *G01T 1/29* (2013.01); *G01T 1/2914* (2013.01); *A61N 2005/1087* (2013.01); *G01H 9/00* (2013.01); *G01H 11/08* (2013.01)

(58) Field of Classification Search
CPC ........................................ G01T 1/29
See application file for complete search history.

(56) References Cited

U.S. PATENT DOCUMENTS

| 8,835,870 | B2 | 9/2014 | Jung et al. |
| 2013/0218009 | A1* | 8/2013 | Balakin ............ A61N 5/1077 600/427 |
| 2013/0261369 | A1 | 10/2013 | Jung et al. |
| 2014/0061493 | A1 | 3/2014 | Prieels et al. |
| 2017/0165504 | A1* | 6/2017 | Dollinger ............ A61N 5/1048 |

OTHER PUBLICATIONS

A.I. Kalinichenko et al., "Radiation-Acoustic Monitoring of Therapeutic Beam", Proceedings of the 2003 Particle Accelerator Conference, 2003, pp. 1080-1082, IEEE.

* cited by examiner

Primary Examiner — James Choi

(57) ABSTRACT

Provided is a method for measuring a depth profile of a particle beam, the method including providing first sensors in a first direction in auditory organs of a human body, providing second sensors in a second direction that intersects with the first direction on a top of a head and in a mouth of the human body, providing a particle beam into the head of the human body, detecting an acoustic signal generated by the particle beam through the first and second sensors, and calculating a depth profile of the first and second directions of the particle beam corresponding to a Bragg peak position of the particle beam in the head using the acoustic signal.

12 Claims, 4 Drawing Sheets

METHOD FOR MEASURING DEPTH PROFILE OF PARTICLE BEAM USING ACOUSTIC SIGNALS GENERATED BY THE PARTICLE BEAM

CROSS-REFERENCE TO RELATED APPLICATIONS

This U.S. non-provisional patent application claims priority under 35 U.S.C. § 119 of Korean Patent Application No. 10-2016-0165324, filed on Dec. 6, 2016, and 10-2017-0153300, filed on Nov. 16, 2017 the entire contents of which are hereby incorporated by reference.

BACKGROUND

The present disclosure herein relates to a method for measuring a particle beam, and more particularly to a method of measuring a depth profile of a particle beam.

Typically, a proton therapy is advantageous in that unnecessary radiation dose for a normal tissue may be reduced, as opposed to an existing radiation therapy. Nevertheless, the proton therapy is disadvantageous in that it is not easy to figure out a dose, or a depth profile or range of a particle beam. When a dose distribution of a particle beam in a body is not accurately known, a therapy plan system may not accurately calculate a dose of the beam to be exposed. For that reason, in a current proton therapy facility, the therapy is proceeded with a margin of an additional planning target volume (PVT) around a therapy site in consideration of safety of a patient. Since a proton beam passes into a human body deeply as much as energy of its own, completely delivers the energy and then is absorbed, it is not possible to predict an internal dose by an exit dose of a proton beam distribution. Even though a positron emission tomography (PET) imaging method has been proposed in which a position at which a positron generated by a proton interacting with an atom or the nucleus that composes the inner body is pair-annihilated is measured, it is pointed out that it is not suitable to check, in real time, a distribution of positron emitting bodies due to the long half-life of the positron generated by nuclear reaction, and a correlation between a dose distribution of the proton beam and a generation position of the positron emission body is small.

On the other hand, there are some cases where the proton beam collides with the nucleus of an atom. In that case, the proton beam loses energy after the collision with the nucleus and the nucleus emits a deuteron, triton, or a heavy ion, or one or more neutrons in some cases. In this process, the nucleus having received energy from the proton emits a gamma ray of high energy (3 to 10 MeV), while transitioning to an excited state and then decaying to a ground state. The gamma ray in such a case is named as a prompt gamma ray after a phenomenon that an emission occurs as soon as a nuclear reaction takes place. As a correlation between a distribution of the prompt gamma ray and the dose distribution of protons is disclosed, a device using the same is being actively developed and a device in a clinical trial stage is also reported.

On the other hand, the proton continuously loses energy in a process where the proton travels the inner body and performs inelastic Coulombic interactions with electrons around an atom. In this process, a phenomenon that the electrons lose energy and are scattered outside the atom appears. It is very well known that when the electron obtains energy, most of the energy is converted to heat energy, and when a temperature change is induced at a specific position or in a space, a sound wave is generated and spreads to surroundings. Recently, there comes an idea of measuring a Bragg peak position and dose information by measuring a sound wave that is generated as a result of interaction of a proton with an electron. When a proton is injected into the body of a patient, an acoustic signal generated in the body spreads at 360 degree angle and reaches the skin. At this point, when a sound sensor is made to physically contact the skin and a correlation is calculated between a time when the proton reaches the skin and a time when the acoustic signal is measured in consideration of a propagation speed of the acoustic signal in the body, the Bragg peak position may be accurately found. However, it is disadvantageous that the number of protons used in the therapy is limited and the intensity of an acoustic signal generated thereby is not so strong to be measured through the skin.

SUMMARY

The present disclosure provides a method for measuring a depth profile of a particle beam, capable of effectively detecting an acoustic signal in the head of a human body.

The present disclosure also provides a method for measuring a depth profile of a particle beam, capable of accurately calculating a Bragg peak position.

An embodiment of the inventive concept provides a method for measuring a depth profile of a particle beam, the method including: providing first sensors in a first direction in auditory organs of a human body; providing second sensors in a second direction that intersects with the first direction on a top of a head and in a mouth of the human body; providing a particle beam into the head of the human body; detecting an acoustic signal generated by the particle beam through the first and second sensors; and calculating a depth profile of the first and second directions of the particle beam corresponding to a Bragg peak position of the particle beam in the head using the acoustic signal.

In an embodiment, the first sensors may include a piezoelectric sensors or optical sensors.

In an embodiment, the first sensors may sense vibrations of eardrums of the auditory organs.

In an embodiment, the first sensors may be provided in middle ears of the auditory organs.

In an embodiment, the second sensors may include piezoelectric sensors.

In an embodiment, the providing of the first sensors may include measuring a first distance between the first sensors, and the providing of the second sensors may include measuring a second distance between the second sensors.

In an embodiment, the particle beam may include a proton beam.

In an embodiment, the particle beam may be incident in a third direction that intersects with the first and second directions.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
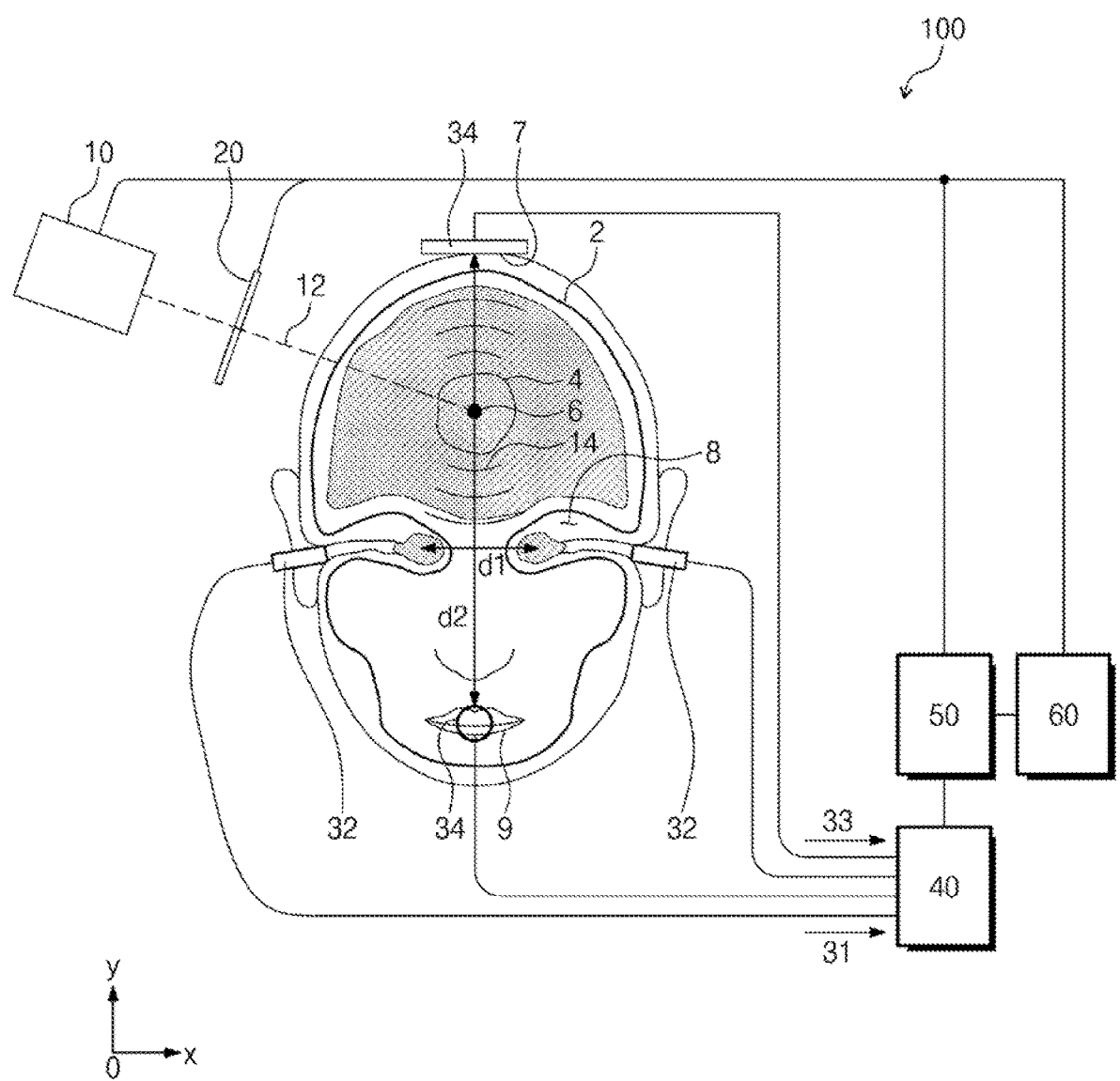
FIG. 1 shows a device for measuring a depth profile of a particle beam.

Hereinafter, exemplary embodiments of the inventive concept will be described in conjunction with the accompanying drawings. The above and other aspects, features, and advantages of the present disclosure will become apparent from the detailed description of the following embodiments in conjunction with the accompanying drawings. However, it should be understood that the present invention is not limited to the following embodiments and may be embodied in different ways. Rather, the embodiments are provided so that so that this disclosure will be thorough and complete and will fully convey the concept of the invention to those skilled in the art, and the present disclosure will only be defined by the appended claims. Like reference numerals indicate like elements throughout the specification and drawings.

The terminology used herein is for the purpose of describing particular embodiments only and is not intended to limit the scope of the present disclosure. As used herein, the singular forms "a", "an" and "the" are intended to include the plural forms as well, unless the context clearly indicates otherwise.

It will be further understood that the terms "comprises," "comprising," "includes" and/or "including," when used in this specification, specify the presence of stated features, integers, operations, elements, and/or components, but do not preclude the presence or addition of one or more other features, integers, steps, operations, elements, components, and/or groups thereof. Also, as just exemplary embodiments, reference numerals shown according to an order of description are not limited to the order.

Moreover, exemplary embodiments are described herein with reference to cross-sectional views and/or plane views that are idealized exemplary illustrations. In the drawings, the dimensions of layers and regions are exaggerated for clarity of illustration. Accordingly, variations from the shapes of the illustrations as a result, for example, of manufacturing techniques and/or tolerances, are to be expected. Thus, exemplary embodiments should not be construed as limited to the shapes of regions illustrated herein but are to include deviations in shapes that result, for example, from manufacturing. Thus, the regions illustrated in the figures are schematic in nature and their shapes are not intended to illustrate the precise shape of a region and are not intended to limit the scope of example embodiments.

FIG. 1 shows a device 100 for measuring a depth profile of a particle beam of the inventive concept.

Referring to FIG. 1, the device 100 for measuring a depth profile of a particle beam may include a particle beam source 10, a hodoscope 20, first sensors 32, second sensors 34, a signal amplifier 40, a signal processor 50, and a signal analyzer 60.

The particle beam source 10 may generate a particle beam 12. The particle beam 12 may be provided into the head 2 of a human body. For example, the particle beam 12 may include a proton beam. The particle beam source 10 may include a proton generator. Although not shown in the drawing, the particle beam source 10 may include a laser device for generating a laser light, and a target for generating a particle beam by the laser light. The target may include a carbon component such as graphene, graphite, or a carbon nanotube, and the inventive concept is not limited thereto and may be variously embodied and practiced.

The hodoscope 20 may be disposed between the particle beam source 10 and the head 2. The hodoscope 20 may detect an incidence time, dose and/or incidence direction of the particle beam 12. The particle beam 12 may pass the hodoscope 12 and then be provided into a tumor 4 in the head 2. The particle beam 12 may have a Bragg peak position and/or point 6 in the tumor 4 and generate an acoustic signal 14. The acoustic signal 14 may be provided into auditory organs 8 in the head 2. For example, the acoustic signal 14 may have an audible frequency of about 16 Hz to about 20 KHz. On the contrary, the particle beam 12 may generate the acoustic signal 14 of a radio frequency above 20 KHz, which is higher than the audible frequency.

The first sensors 32 may be provided in the head 2 of the human body. According to an embodiment, the first sensors 32 may be disposed in a first direction x in the auditory organs 8 of the head 2. For example, the first sensors 32 may be provided in the opposite earholes of the head 2. The first sensors 32 may sense the acoustic signal 14 to generate a first sensing signal 31. The first sensing signal 31 may provide information about the Bragg peak position 6 for the first direction x. For example, the first sensor 32 may include a piezoelectric sensor, optical sensor, photodiode, or optical fiber acoustic sensor.

The second sensors 34 may be disposed in the head 2 of the human body in a second direction y. For example, the second sensor 34 may be disposed on the top of the head 2 and in the mouth 9. The second sensors 34 may sense the acoustic signal 14 to generate second sensing signals 33. The second sensing signals 33 may provide information about the Bragg peak position 6 for the second direction y. For example, the second sensor 34 may include a piezoelectric sensor.

The signal amplifier 40 may be connected to the first and second sensors 32 and 34. The signal amplifier 40 may amplify the first and second sensing signals 31 and 33 from the first and second sensors 32 and 34.

The signal processor 50 may be connected to the hodoscope 20 and the signal amplifier 40. According to an example, the signal processor 50 may process information from the particle beam 12 and the acoustic signal 14. The signal processor 50 may receive detection signals from the particle beam 12, and the first and second sensing signals 31 and 33. The signal processor 50 may determine the dose and incidence direction of the particle beam 12. The signal processor 50 may determine a frequency, phase, and strength of each of the first and second sensing signals 31 and 33.

The signal analyzer 60 may be connected to the signal processor 50. The signal analyzer 60 may calculate and/or determine the Bragg peak position 6 of the particle beam 12 for the first and second directions x and y by using the incidence direction of the particle beam 12 and a phase difference between the first and second sensing signals 31 and 33. In addition, the signal processor 60 may determine an absorption dose of the particle beam 12 by using the strengths of the first and second sensing signals 31 and 33. In contrast, the signal processor 50 and the signal analyzer 60 may be configured from one computer. A method for calculating the Bragg peak position 6, the depth profile of the particle beam 12, and/or the absorption dose of the particle beam 12 by the signal processor 50 and the signal analyzer 60 will be described in detail in the following.

A depth profile measuring method of a device 100 for measuring a depth profile of the particle beam 12 configured in this way will be described in detail.

Figure 2:
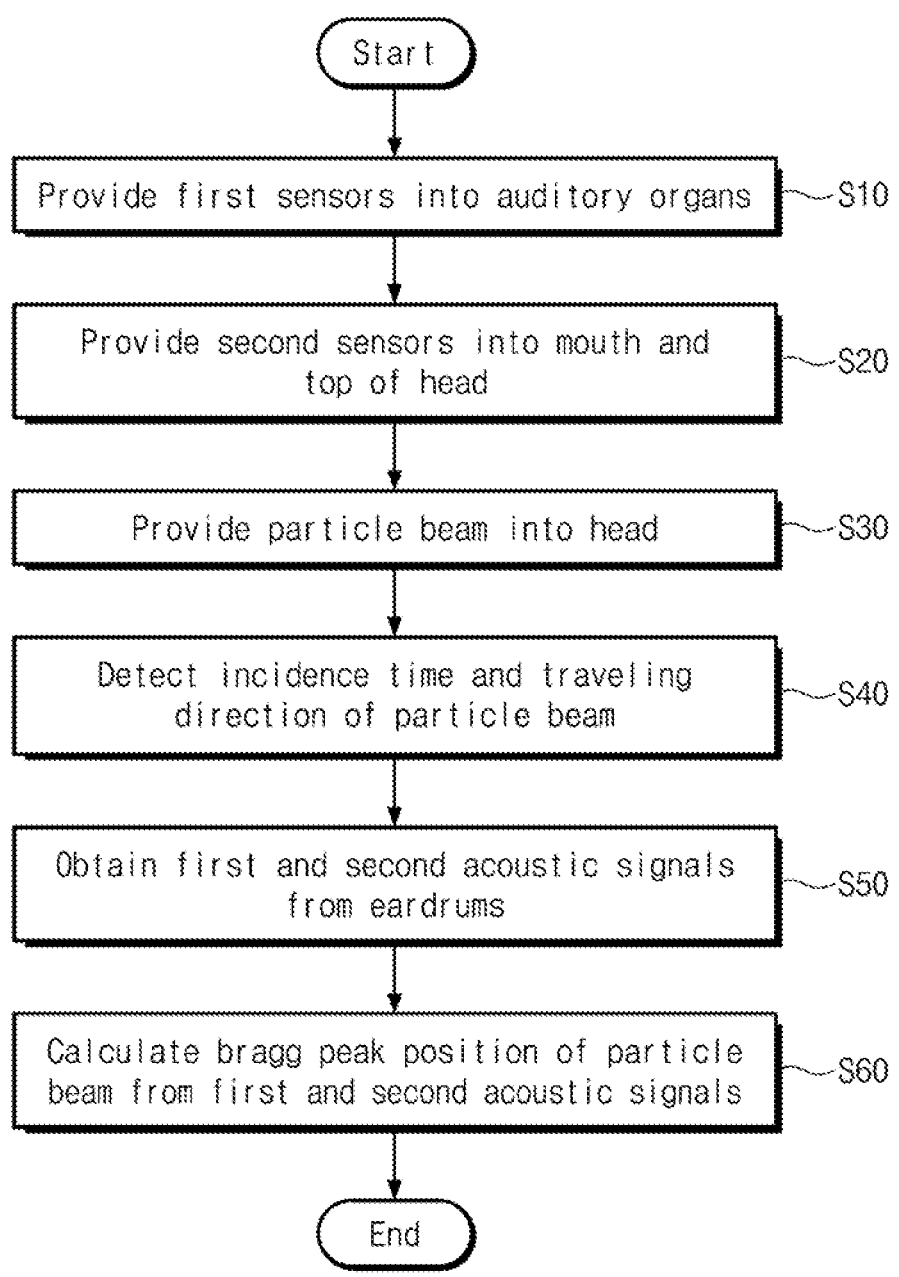
FIG. 2 is a flowchart showing a method for measuring a depth profile of a particle beam 12 according to the inventive concept.

FIG. 2 shows a method of measuring a depth profile of the particle beam 12 according to the inventive concept.

Referring to FIG. 2, the depth profile measuring method of the particle beam 12 may include providing the first sensors 32 in the auditory organs 8 of a human body (operation S10), providing the second sensors 34 in the mouth 9 and the top of the head (operation S20), providing the particle beam 12 into the head 2 of the human body (operation S30), detecting an incidence time and traveling direction of the particle beam 12 (operation S40), obtaining the first and second sensing signals 31 and 33 (operation S50), and calculating the Bragg peak position 6 of the particle beam 12 in the head 2 from the first and second sensing signals 31 and 33 (operation S50).

Referring to FIGS. 1 and 2, the first sensors 32 are provided in the auditory organs 8 of both sides of the head 2 (operation S10). The first sensors 32 may be provided in the auditory organs 8 by an operator and/or robot in the first direction x. The signal processor 50 and/or the signal analyzer 60 may detect a first distance d1 between the first sensors 32. The first distance d1 may be detected through short-range communication such as Bluetooth. For example, each of the auditory organs 8 may be divided into an external ear, a middle ear, and an internal ear in a depth direction. The external ear may be defined as a part closed to the ear protruding out from the head, the internal ear as a part farthest away from the ear, and the middle ear as a part connecting between the external and internal ears.

Figure 3:
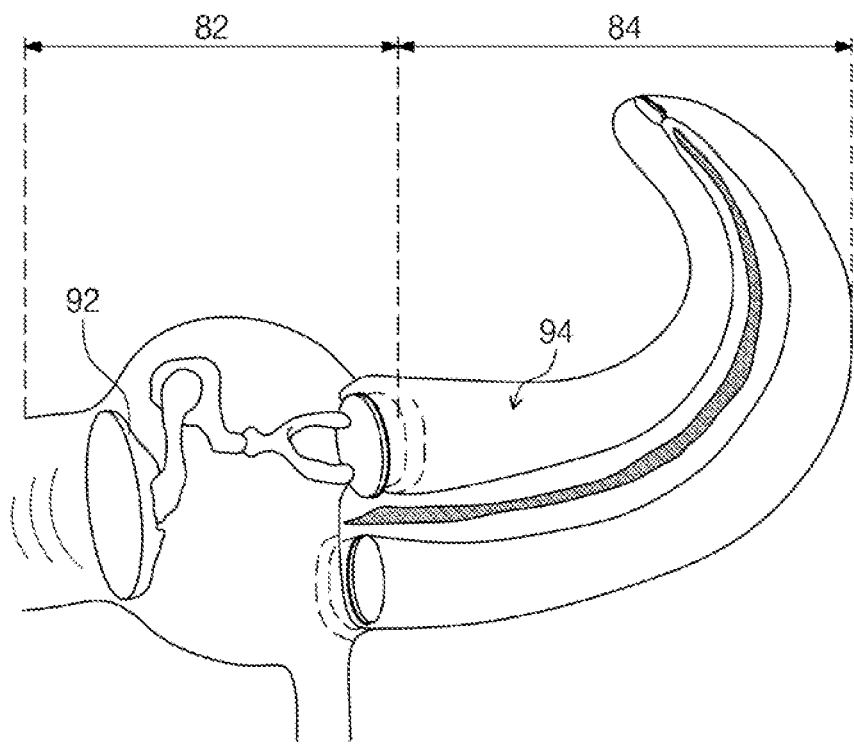
FIG. 3 shows an eardrum and a cochlea respectively in the middle ear and the internal ear of the auditory organ of FIG. 1.

FIG. 3 shows respectively an eardrum 92 and the cochlea 94 in the middle ear 82 and the internal ear 84 of the auditory organ of FIG. 1. Referring to FIGS. 1 and 3, the eardrum 92 is disposed in the middle ear 82 and the cochlea 94 may be disposed in the internal ear 84. The eardrum 92 may have a thin plate form. The eardrum 92 may convert a sound outside the auditory organ 8 to an external acoustic vibration, and deliver the external acoustic vibration to the brain in the head 2 through the cochlea 94. The cochlea 94 may be filled with a gas and/or fluid. In addition, the eardrum 92 may convert the acoustic signal 14 in the cochlea 94 to an internal sound, and discharge the internal sound outside the auditory organ 8. The acoustic signal 14 and the internal sound may correspond to electromagnetic energy. Hereinafter, both the acoustic sound 14 and the internal sound will be described as the acoustic signal 14.

According to an embodiment, each of the first and second sensors 32 and 34 may be provided in the middle ear 82.

Then, the second sensors 34 are provided on the top 7 of the head and in the mouth 9 (operation S20). The second sensors 34 may be provided on the top 7 and/or crown of the head and in the mouth 9 by an operator and/or robot in the second direction y. The signal processor 50 and/or the signal analyzer 60 may detect a second distance d2 between the second sensors 34. The second distance d2 may be detected through short-range communication such as Bluetooth.

Then, the particle beam source 10 provides the particle beam 12 into the head 2 through the hodoscope 20 (operation S30). The particle beam 12 may be incident in a third direction (not shown) with an arbitrary dose.

Then the hodoscope 20 detects the dose and traveling direction of the particle beam (operation S40). The hodoscope 20 may transmit a detection signal of the particle beam 12 to the signal analyzer 50. The signal processor 50 may control the particle beam 10. The particle beam 12 in the head 2 may be provided into the tumor 4. The particle beam 12 may be absorbed at the Bragg peak position 6 in the tumor 4 and generate the acoustic signal 14. The acoustic signal 14 may be delivered to the auditory organs 8.

Thereafter, the first and second sensors 32 and 34 sense the acoustic signal 14 (operation S50). The first sensors 32 may sense the acoustic signal 14 at the eardrum 92 in the middle ear 82. The sensing method of the acoustic signal 14 is as the following.

Figure 4A:
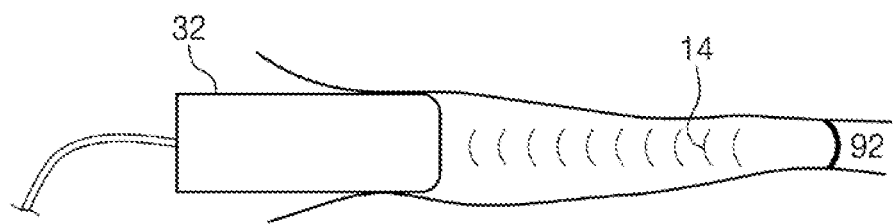
FIGS. 4A and 4B show methods of detecting, by the first sensor of FIG. 1, eardrum vibration.
Figure 4B:
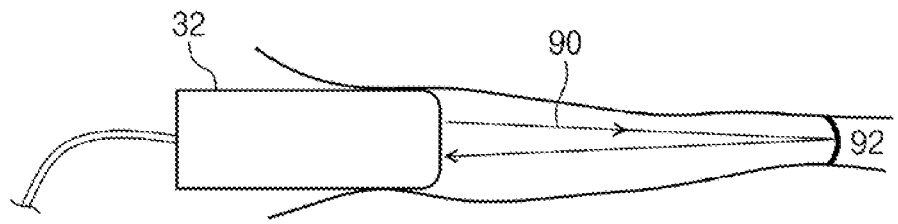

FIGS. 4A and 4B show a method of sensing the acoustic signal 14 at the eardrum 92 by the first sensor 32 of FIG. 1. Referring to FIG. 4A, the first sensor 32 of a piezoelectric element may directly sense the acoustic signal 14 at the eardrum. The eardrum 92 may provide the acoustic signal 14 to the first sensor 32 through the air in an earhole.

Referring to FIG. 4B, the first sensor 32 may sense the vibration of the eardrum 92 with light 90. The second sensor 34 may sense the vibration of the eardrum 92 with the same light 90 as that for the first sensor 32. For example, the first sensor 32 may include an optical source and an optical sensor. Although not shown in the drawing, the optical source may provide the light 90 to the eardrum 92. The optical sensor may sense the light 90 reflected by the eardrum 92.

Referring to FIG. 1 again, the second sensors 34 may directly sense the acoustic signal 14 on the top 7 of the head and in the mouth 9.

In addition, the signal analyzer 60 analyzes the sensed first and second sensing signals 31 and 33 and calculates the depth profile of the particle beam 12. For example, the signal analyzer 60 may calculate the Bragg peak position 6 in the first direction x by using the first sensing signal 31. In detail, the signal analyzer 60 may obtain the Bragg peak position 6 in the first direction x from the first sensing signal 31. On the contrary, the signal analyzer 60 may obtain the Bragg peak position 6 within the first distance d1. In addition, the signal analyzer 60 may calculate the Bragg peak position 6 in the second direction y by using the second sensing signal 33. The signal analyzer 60 may obtain the Bragg peak position 6 for the second direction y from the second sensing signal 33. On the contrary, the signal analyzer 60 may obtain the Bragg peak position 6 within the second distance d2.

The method of measuring a depth profile of a particle beam according to the inventive concept may effectively detect acoustic signals and calculate a Bragg peak position of a particle beam for first and second directions by using the acoustic signals.

As described above, the drawings and embodiments are disclosed in the specification. Herein, specific terms have been used, but are just used for the purpose of describing the inventive concept and are not used for defining the meaning or limiting the scope of the inventive concept, which is disclosed in the appended claims. Thus it would be appreciated by those skilled in the art that various modifications and other equivalent embodiments can be made. Therefore, the true technical scope of the inventive concept shall be defined by the technical spirit of the appended claims.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A method for measuring a depth profile of a particle beam, the method comprising:

providing first sensors in a first direction in auditory organs of a human body, the first sensors sensing vibrations of eardrums of the auditory organs;

providing second sensors in a second direction, the second direction intersecting with the first direction, on a top of a head and in a mouth of the human body;

providing a particle beam into the head of the human body;

detecting, using the first sensors and the second sensors, an acoustic signal generated by the particle beam; and calculating a depth profile of the first and second directions of the particle beam corresponding to a Bragg peak position of the particle beam in the head using the acoustic signal, wherein the first sensors comprise optical sensors, and wherein the second sensors comprise piezoelectric sensors.

2. The method according to claim 1, wherein the first sensors are provided in middle ears of the auditory organs.

3. The method according to claim 1, wherein the providing of the first sensors comprises measuring a first distance between the first sensors, and the providing of the second sensors comprises measuring a second distance between the second sensors.

4. The method according to claim 1, wherein the particle beam comprises a proton beam.

5. The method according to claim 1, wherein the particle beam is incident in a third direction that intersects with the first and second directions.

6. A device comprising:

first sensors configured to be placed in a first direction in auditory organs of a human body, to sense vibrations of eardrums of the auditory organs corresponding to acoustic signals generated by a particle beam being provided into a head of the human body, and to produce respective outputs corresponding to the vibrations;

second sensors configured to be placed in a second direction, the second direction intersecting with the first direction, on a top of a head and in a mouth of the human body and produce respective outputs corresponding to the acoustic signal; and a signal processor configured to calculate, using the outputs of the first sensors and the outputs of the second sensors, a depth profile of the first and second directions of the particle beam corresponding to a Bragg peak position of the particle beam in the head.

7. The device of claim 6, wherein the first sensors comprise piezoelectric sensors or optical sensors.

8. The device of claim 6, wherein the first sensors are provided in middle ears of the auditory organs.

9. The device of claim 6, wherein the second sensors comprises piezoelectric sensors.

10. The device of claim 6, wherein the signal processor calculates the depth profile of the first and second directions of the particle beam according to a first distance between the first sensors and a second distance between the second sensors.

11. The device of claim 6, wherein the particle beam comprises a proton beam.

12. The device of claim 6, wherein the particle beam is incident in a third direction that intersects with the first and second directions.

* * * * *